(12) United States Patent
Day

(10) Patent No.: US 9,036,146 B2
(45) Date of Patent: *May 19, 2015

(54) MICRO PURGE OF PLASMA REGION

(71) Applicant: SCIAPS, INC., Woburn, MA (US)

(72) Inventor: David Day, Boxford, MA (US)

(73) Assignee: SciAps, Inc., Woburn, MA (US)

( * ) Notice: Subject to any disclaimer, the term of this patent is extended or adjusted under 35 U.S.C. 154(b) by 53 days.

This patent is subject to a terminal disclaimer.

(21) Appl. No.: 13/746,095

(22) Filed: Jan. 21, 2013

(65) Prior Publication Data

US 2014/0204375 A1     Jul. 24, 2014

(51) Int. Cl.
    *G01J 3/30*      (2006.01)
    *G01J 3/443*     (2006.01)

(52) U.S. Cl.
    CPC ........................ *G01J 3/443* (2013.01)

(58) Field of Classification Search
    USPC ................................. 356/300–334
    See application file for complete search history.

(56) References Cited

U.S. PATENT DOCUMENTS

| | | | |
|---|---|---|---|
| 5,473,162 A | 12/1995 | Busch et al. | |
| 5,520,679 A | 5/1996 | Lin | |
| 6,355,908 B1 | 3/2002 | Tatah et al. | |
| 6,801,595 B2 | 10/2004 | Grodzins et al. | |
| 7,233,643 B2 | 6/2007 | Sipila et al. | |
| 7,394,537 B1 | 7/2008 | Lindfors et al. | |
| 8,184,287 B2 | 5/2012 | Hamilton et al. | |
| 2003/0010907 A1 | 1/2003 | Hayek et al. | |
| 2003/0174325 A1 | 9/2003 | Zhang et al. | |
| 2003/0234928 A1 | 12/2003 | Lucas et al. | |
| 2004/0183010 A1 | 9/2004 | Reilly et al. | |
| 2005/0068524 A1 | 3/2005 | Wu et al. | |
| 2005/0236563 A1 | 10/2005 | Busch et al. | |
| 2006/0100676 A1 | 5/2006 | Walmsley | |
| 2006/0262302 A1* | 11/2006 | Eklin ............................ 356/318 |
| 2007/0265783 A1 | 11/2007 | Mound | |
| 2008/0151241 A1 | 6/2008 | Lindfors et al. | |
| 2008/0165344 A1 | 7/2008 | Treado et al. | |
| 2008/0259330 A1 | 10/2008 | Dillon et al. | |
| 2009/0007933 A1 | 1/2009 | Thomas et al. | |
| 2010/0197116 A1 | 8/2010 | Shah et al. | |
| 2012/0044488 A1 | 2/2012 | Senac | |
| 2012/0162642 A1 | 6/2012 | Watson et al. | |

(Continued)

FOREIGN PATENT DOCUMENTS

WO    WO 2012/135961 A1    10/2012
WO    WO 2013083950        6/2013

OTHER PUBLICATIONS

U.S. Appl. No. 13/746,012, Day.

(Continued)

*Primary Examiner* — Abdullah Nur
(74) *Attorney, Agent, or Firm* — Iandiorio Teska & Coleman, LLP

(57) ABSTRACT

An analysis system includes a laser source generating a laser beam for creating a plasma at a location on a sample. A spectrometer is responsive to photons emitted by the sample at said location and has an output. At least one nozzle is configured to deliver inert gas from a source locally to the location on the sample. A controller is responsive to a trigger signal and is configured to activate the laser source generating a series of laser pulses, open a valve to purge the location locally on the sample, and close the valve after one or more laser pulses.

3 Claims, 12 Drawing Sheets

(56) References Cited

U.S. PATENT DOCUMENTS

| | | | |
|---|---|---|---|
| 2012/0268743 A1 | 10/2012 | Wang et al. | |
| 2012/0314214 A1 | 12/2012 | Alexander et al. | |
| 2014/0022531 A1 | 1/2014 | Sackett | |
| 2014/0022532 A1 | 1/2014 | Sackett | |
| 2014/0204378 A1* | 7/2014 | Day ............................. | 356/326 |

OTHER PUBLICATIONS

U.S. Appl. No. 13/746,102, Day.
U.S. Appl. No. 13/746,108, Day.
U.S. Appl. No. 13/746,110, Day.
U.S. Appl. No. 14/179,670, Day et al.
Written Opinion of the International Searching Authority for PCT Application No. PCT/US2014/11961 mailed May 8, 2014 (six (6) pages).
Written Opinion of the International Searching Authority for PCT Application No. PCT/US2014/11863 mailed May 13, 2014 (nine (9) pages).
Oxford Instruments, Laser Induced Breakdown Spectroscopy (LIBS), http://www.oxford-instruments.com/products/spectrometers/laser-induced-bre..., (two (2) pages), 2014.
Applied Spectra, Inc., Model RT100-EC, http://www.appliedspectra.com/products/rt100-ec.html, (four (4) pages), 2013.
RMG Technology Introduces Hand-Held Laser Analyzer, Recycling Today, http://www.recyclingtoday.com/Article.aspx?article id=141665 (two (2) pages), 2013.
Ocean Optics, Laser-Induced Breakdown Spectroscopy, The LIBS2500plus LIBS Systems, http://www.oceanoptics.com/products/libs.asp, (four (4) pages), 2012.
Applied Photonics, LIBSCAN 25, brochure, (two (2) pages), 2010.
Written Opinion of the International Searching Authority for PCT Application No. PCT/US2014/16188 mailed Feb. 2, 2015 (eight (8) pages).
Written Opinion of the International Searching Authority for PCT Application No. PCT/US2014/12060 mailed Jan. 27, 2015 (five (5) pages).

* cited by examiner

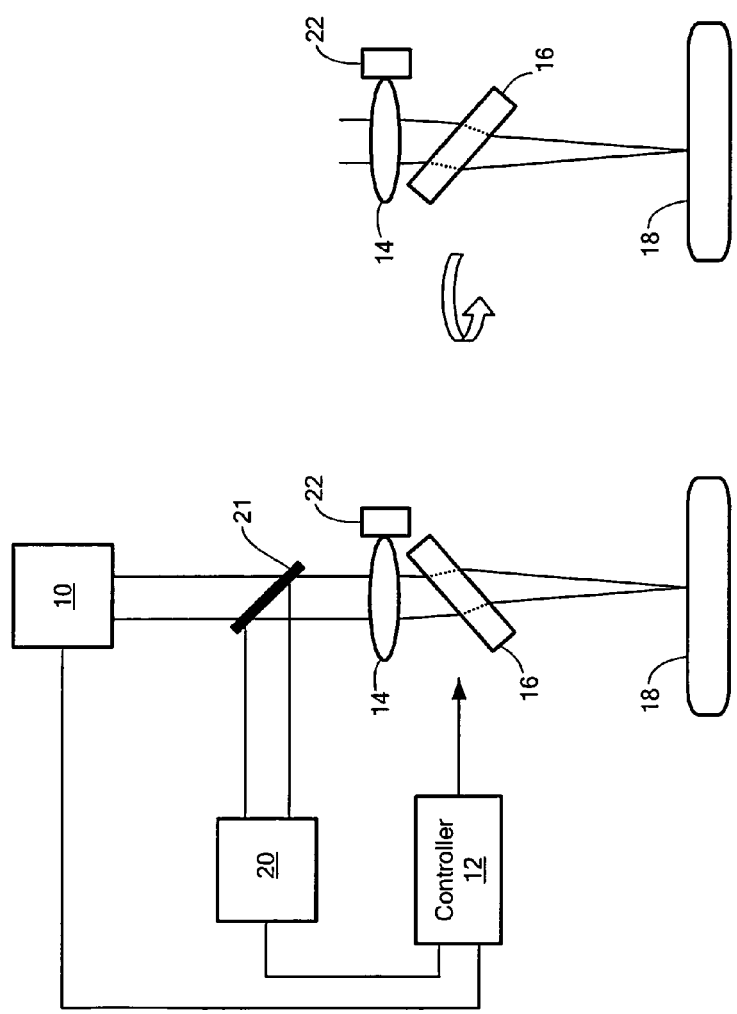

MICRO PURGE OF PLASMA REGION

FIELD OF THE INVENTION

The subject invention relates to spectroscopic instruments.

BACKGROUND OF THE INVENTION

Various spectroscopic instruments are known. X-ray based instruments, for example, can be used to determine the elemental make up of a sample using x-ray florescence spectroscopy. Portable XRF has become a preferred technique for elemental analysis in the field. Portable XRF is fast, non-destructive, and provides reasonably accurate results (i.e., quantification of elemental concentrations in a wide variety of samples). With XRF, an x-ray tube is used to direct x-rays at a sample. Atoms in the sample absorb x-rays and re-emit x-rays that are unique to the atomic structure of a given element. A detector measures the energy of each x-ray and counts the total number of x-rays produced at a given energy. From this information, the types of elements and the concentration of each element can be deduced. Commercially available analyzers include the Delta manufactured by Olympus NDT and the Niton XLT-3 manufactured by Thermo Fisher Scientific.

X-rays, however, pose a safety concern. Also, portable and benchtop XRF analyzers have not to date been used to determine lower atomic number elements such as beryllium, sodium, carbon, boron, oxygen, nitrogen, lithium, and the like.

Laser induced break down spectroscopy (LIBS) devices are known and used to detect the elemental concentration of lower atomic numbered elements with some accuracy. These devices typically include a high powered laser that sufficiently heats a portion of the sample to produce a plasma. As the plasma cools, eventually the electrons return to their ground states. In the process, photons are emitted at wavelengths unique to the specific elements comprising the sample. The photon detection and subsequent measurement of elemental concentrations are similar to spark optical emission spectroscopy (OES). Examples of LIBS devices are the LIBS SCAN 25 from Applied Photonics, the LIBS25000 from Ocean Optics, and the RT 100 from Applied Spectra.

Some elements such as carbon, phosphorous, and sulfur react with oxygen resulting in a very low level signal which can be difficult to detect and/or properly analyze.

It is known to use an inert gas such as argon to purge the sample. Typically, the flow rate is high and the area purged is large. The gas may be used to purge a sample chamber in some prior art LIBS analysis systems. Accordingly, a large source (e.g., a tank) of argon gas is required and must be toted along in the field. Other analysis systems using an argon purge, such as a mobile spark OES analyzer, also use quite a lot of argon gas for purging.

SUMMARY OF THE INVENTION

In a LIBS device, it is desirable to use eye-safe lasers. One example of an eye-safe laser with enough power for LIBS usage is one at 1.5 micron wavelength. Other wavelengths are possible. Water absorbs heavily at this wavelength thus preventing the laser reaching the retina of the eye. Devices with eye-safe lasers receive a regulatory rating of either Class 1 or Class 2 depending upon the power level of the laser. Class 1 is the most desired because it is the least regulated. For handheld devices which operate in an open beam configuration, the Class 1 or Class 2 rating is highly desired because it yields the maximum operator safety and is subject to the least amount of regulation.

Because of the lower pulse energies currently available from 1.5 μm lasers, it is often necessary to focus the laser into a smaller spot size, typically 100 μm or less in order to get a high enough power density to ignite a plasma. Lower power lasers than are commonly used for bench top LIBS instruments are also desirable particularly in the case of a handheld or portable LIBS unit due to size and power restrictions imposed to maintain portability of the instrument. The very small beam spot size on the sample creates three problems that should be solved to make a LIBS device commercially viable. First, the laser must be focused precisely on the surface of the sample being analyzed for consistent analytical results. Second, the sample must be clean from surface contamination including oxidation on the same distance scale of 100 μm or less. Third, some samples are non-homogeneous. Thus, on a sample, locations even a small distance away from each other my yield different elements and/or different elemental concentrations. It is therefore desirable to design such a LIBS device to make several measurements at different regions of the sample and combine the results. The invention disclosed includes an eye-safe laser in one preferred embodiment. However, the invention is useful for lasers of other wavelengths and/or larger beam spots on the sample.

In one preferred example, a spectrometer system, preferably handheld or otherwise portable, is provided and is configured to automatically, based on spectral information, properly focus the laser on the sample, clean the sample, and analyze different locations on the sample.

In a portable, battery powered device, it is not desirable to require the user to carry a large tank of purge gas. In one preferred embodiment, a purge subsystem allows a small argon cartridge to be used (e.g., 3-6" long) because the purge gas is conserved. The flow rate during testing is low and the gas flow is directed only locally to the location on the sample where the plasma is generated by the laser beam. Moreover, the purge gas is supplied only just before testing and turned off at the end of a test (or even before). In this way, the purge gas is further conserved.

Featured is an analysis system comprising a laser source generating a laser beam for creating a plasma at a location on a sample, a spectrometer responsive to photons emitted by the sample at the location and having an output, and at least one nozzle configured to deliver inert gas from a source locally to the location on the sample. A valve is located between a source of inert gas and the nozzle. A trigger mechanism generates a trigger signal. A controller is responsive to the trigger signal and is configured to activate the laser source generating a series of laser pulses, to open the valve to purge the location locally on the sample, and to close the valve after one or more laser pulses.

The controller may be configured to process the spectrometer output between pulses. In some examples, the nozzle is positioned and configured to produce an inert gas purge spray having a volume less than 1.0 cm$^3$. The nozzle is preferably configured to produce an inert gas spray at a flow rate of less than 2 CFH. The controller is preferably configured to open the valve to purge the location locally on the sample before and proximate the first laser pulse.

The source of inert gas may be a cartridge. In some embodiments, the analysis system is a portable, battery powered unit and the gas cartridge is loadable within the unit.

A battery powered, portable LIBS analyzer in accordance with examples of the invention include a laser source generating a laser beam for creating a plasma at a location on a sample, a spectrometer responsive to photons emitted by the sample at the location and having an output, cartridge of inert gas, and a nozzle configured to deliver inert gas from the cartridge locally to the location on the sample in a volume less than 1.0 cm$^3$ and at a flow rate of less than 2 CFH. A valve is disposed between the cartridge of inert gas and the nozzle. A trigger mechanism generates a trigger signal. A controller is responsive to the trigger signal and is configured to activate the laser source generating a series of laser pulses, to open the valve to purge said location locally on the sample prior to and proximate a first laser pulse, and to close the valve after one or more laser pulses. The cartridge may be loadable with the analyzer.

One analysis method includes activating a laser source to generate a series of laser pulses striking a sample at a location, directing an inert gas at said location, and delivering said inert gas to said location at a predetermined flow rate and at a predetermined volume prior to and proximate the first laser pulse. In one example, the predetermined flow rate is less than 2 CFH, the predetermined volume is less than 1.0 cm$^3$, and the inert gas is delivered less than 0.5 seconds before the first laser pulse.

Also featured is a method making an analysis system. A laser source generates a laser beam for creating a plasma at a location on a sample. The method includes configuring at least one spectrometer to be responsive to photons emitted by the sample at said location, including at least one nozzle to deliver inert gas from a source locally to said location on the sample, and incorporating a valve between a source of inert gas and the nozzle. The method also includes programming a controller to be responsive to a trigger signal and to activate the laser source generating a series of laser pulses, open the valve to purge said location locally on the sample, and close the valve after one or more laser pulses.

The controller can be further configured to process a spectrometer output between pulses. Preferably, the nozzle is positioned and configured to produce an inert gas purge spray having a volume less than 1.0 cm$^3$, to produce an inert gas spray at a flow rate of less than 2 CFH.

Featured is an analysis system comprising a moveable focusing lens, a laser having an output directed at the focusing lens, a spectrometer outputting intensity data from a sample. A controller system is responsive to the spectrometer and is configured to energize the laser, process the output of the spectrometer, and adjust the position of the focusing lens relative to the sample until the spectrometer output indicates a maximum or near maximum intensity resulting from a laser output focused to a spot on the sample. In this manner, an eye safe laser may be used.

In some embodiments, the detection path is through the focusing lens to the spectrometer. The laser output wavelength may be approximately 1.5 µm. The laser may be as low as class 1 laser with a focused spot size equal to or less than 100 µm on the sample.

The intensity is preferably an integrated intensity over a plurality of wavelengths. Adjusting the position of the focusing lens may include moving it away from the sample and towards the sample.

Also featured in some example is a moveable optic configured to direct focused laser energy to multiple locations on the sample. The controller system may further be configured to initiate a moving spot cycle wherein the orientation of the moveable optic is adjusted and again the laser is energized and the output of the spectrometer processed. The controller system may be configured to terminate the moving spot cycle when the spectrometer output does not change by a predetermined amount between different sample locations. Preferably, the controller system is configured to adjust the position of the focusing lens at each sample location. In one example, the movable optic includes the focusing lens. In other examples, the movable optic includes one or more mirrors or a glass optic.

In some examples, the controller system may be configured to initiate a cleaning cycle and to terminate the cleaning cycle—processing the spectrometer output and energizing the laser in a cleaning mode until the output stabilizes. The cleaning cycle may automatically terminate when a rolling average of at least one peak intensity changes by less than a predetermined percentage. The controller can be configured to move the position of the focusing lens producing a larger spot size during the cleaning cycle and to return the focusing lens to a focused position after terminating the cleaning cycle Also featured is an analysis system comprising an adjustable focusing lens, a laser having an output directed at the focusing lens, a moveable component configured to direct laser energy to multiple locations on a sample, and a spectrometer outputting intensity data from the sample. A controller system is responsive to the spectrometer and is configured to initiate a focusing cycle wherein the laser is energized, the spectrometer output is analyzed, and the position of the focusing lens is adjusted until the spectrometer output is optimized resulting from a laser output focused on the sample. The system initiates a cleaning cycle wherein the laser is energized, the spectrometer output is analyzed, and the cleaning cycle terminates when the spectrometer output stabilizes. The system initiates a moving spot cycle wherein the movable component is adjusted and the spectrometer output is analyzed for multiple locations on the sample.

Also featured is an analysis method comprising energizing a laser producing a beam impinging on a sample, analyzing the resulting photons, and based on the analysis, automatically adjusting the focus of the laser beam on the sample to produce a focused spot on the sample. The focus of the laser beam may be adjusted until a maximum or near maximum intensity is reached at one or more wavelengths. Photons may be directed from the sample along a detection path through the focusing lens to a detector system.

The method may further include cleaning the sample using the laser beam. Cleaning can include adjusting the focus of the laser to produce a larger spot. Cleaning the sample may include energizing the laser, analyzing the resulting photons, and terminating cleaning when an intensity stabilizes.

One method may include moving the beam to multiple locations on the sample and optionally adjusting the focus of the laser beam at each location. The method may include cleaning the sample at each location using the beam. The beam can be moved until analysis of the sample indicates a homogeneous sample. For a non-homogeneous sample, the beam may be moved a predetermined maximum number of times.

Also featured is a spectroanalysis method comprising directing a laser output at an adjustable focusing lens, detecting intensity data from the sample, and initiating a focusing cycle wherein the laser is energized, the intensity data is analyzed, and the position of the focusing lens is adjusted until the intensity data is optimized resulting in a laser output focused on the sample. A cleaning cycle is initiated wherein the laser is energized, the intensity data is analyzed, and the cleaning cycle terminates when the intensity data stabilizes. A moving spot cycle is initiated wherein the laser output is moved to a new location on the sample and the intensity data is analyzed for multiple locations on the sample.

In some examples, the focusing lens may be adjusted to make the predetermined spot larger during the cleaning cycle.

The focusing cycle and cleaning cycle may be initiated for each location on the sample during the moving spot cycle. In one example, the moving spot cycle terminates when the intensity data indicates the sample is homogeneous.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIGS. 3A and 3B are block diagrams showing still another example of a spectrometer system in accordance with the invention;

DETAILED DESCRIPTION OF THE INVENTION

Figure 1:
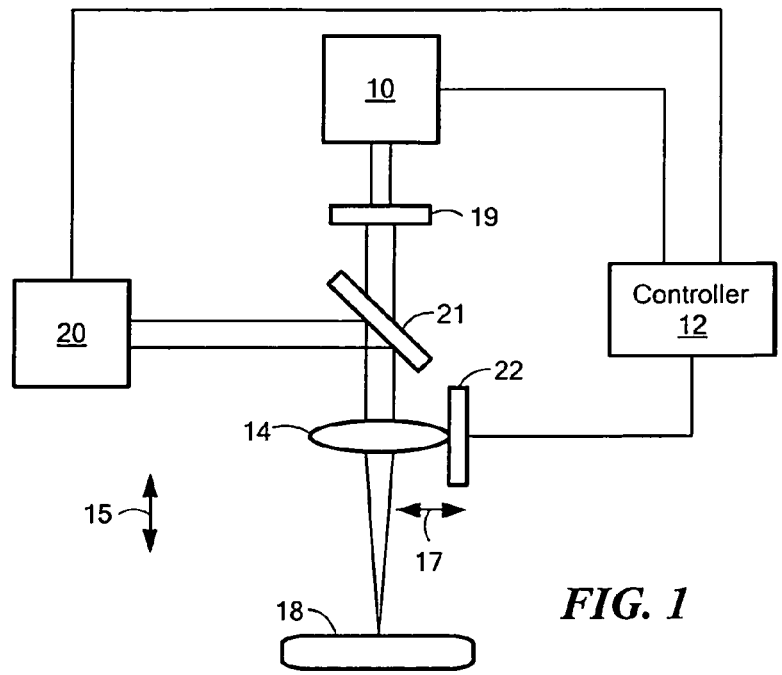
FIG. 1 is a block diagram showing an example of a spectrometer system in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In the example of FIG. 1, a LIBS laser 10 directs its collimated output, when energized by controller subsystem 12, to adjustable focusing lens 14 which produces a small spot (e.g., 100 μm) of laser energy on sample 18 creating a plasma. The focusing lens can be moved in the axial direction, meaning in a direction perpendicular to the surface either closer to or further from the sample as shown by arrow 15.

The resulting photons of the plasma produced by the laser energy proceed along a detection path including focusing lens 14 to subsystem 20 (e.g., a spectrometer). The output signal of detector subsystem 20 may be processed by controller subsystem 12.

In this particular example, high pass filter 21 passes laser energy (e.g., at, for example, 1500 nm) from LIBS laser 10 to lens 14 and reflects lower wavelengths (e.g., below about 1,000 nm) to subsystem 20 which may include a slit.

A translation mechanism 22 may be provided under the control of controller subsystem 12 to move focusing lens 14 in the axial direction towards or away from the sample surface (vertically in the figure) in order to permit focusing control for rough sample surfaces as well as to compensate for any path length variations introduced by the optics. A stepper motor combined with gears and the like can be used to adjust the position of focusing lens 14. An electromagnetic coil or other means of translation may also be used.

Spectrometer 20 may include a CCD detector array as set forth in the design of co-pending application Ser. Nos. 13/591,907 and 13/507,654 incorporated herein by this reference. Other spectrometers include echelle (with a 2D CCD), Paschen-Runge, and the like.

Controller subsystem 12 may include one or more microprocessors, digital signal processors, analog and/or digital circuitry or similar components, and/or application specific integrated circuit devices and may be distributed (e.g., one micro-processor can be associated with the detector subsystem while a micro-controller can be associated with the device's electronic circuit board(s). The same is true with respect to the algorithms, software, firmware, and the like. Various electronic signal processing and/or conditioning and/or triggering circuitry and chip sets are not depicted in the figures. Additional optics including beam expansion, collimation, and/or adjustment optics are possible in some examples. Beam expansion optic 19 is shown for increasing the diameter of the laser output impinging on focusing lens 14. Laser 10 is preferably a class 1 eye safe laser.

Mechanism 22 may also be configured to move focusing lens 14 right and left in the figure as shown by arrow 17 (and/or in a direction in and out of the plane of FIG. 1) to move the laser beam spot to multiple locations on the sample. In one example, controller 12 is configured to automatically focus the laser beam on the sample, clean the sample, analyze the sample, and then move the laser beam and again properly focus the beam, clean the new location, and again analyze the sample. These features are discussed below.

Figure 2:
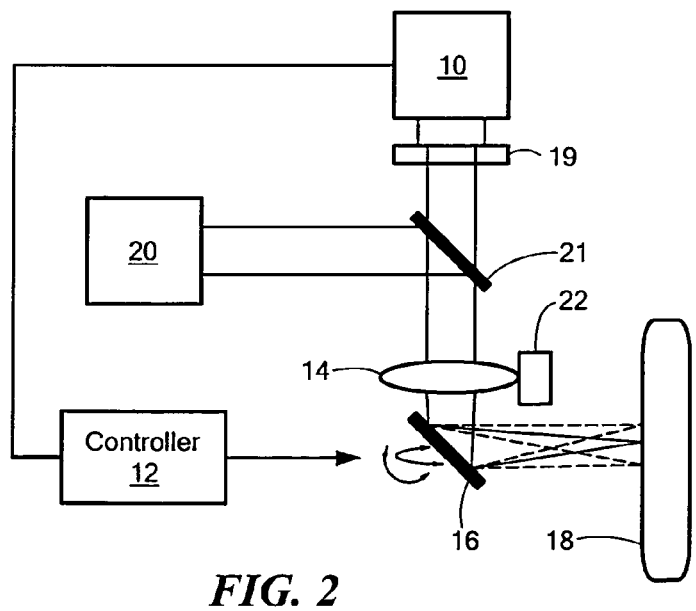
FIG. 2 is a block diagram showing another example of a spectrometer system in accordance with the invention.

Another way to move the laser beam to multiple locations on the sample is to use adjustable optic 16, FIG. 2. Optic 16 may include a tip-tilt mirror electromagnetically or electrostatically driven, MEMS mirrors, and the like such as those available from Mirrorcle Technologies, Thor Labs, Newport, as well as other suppliers.

In FIG. 3B, the delivery and return optical paths are similar to those described for FIG. 1. This example includes a rotating glass window (optic 16) as an alternative method for implementing spot translation on the sample. The change in refractive index between free space and the glass window combined with the angle of the glass window relative to the optical axis results in a lateral shift of the laser beam as shown in FIGS. 3A and 3B. Rotating the glass around a glass optic 5 mm thick with a refractive index of 1.5 for example, may be used. If the glass surface is angled at 55° to the optical axis, the lateral displacement would be approximately 2.2 mm. By rotating the glass optic around the optical axis as shown in FIGS. 3A and 3B, the focus spot would follow a circle of radius 2.2 mm on the sample surface (e.g., a circle circumference of approximately 14 mm). If the glass optic is rotated about the optical axis in 6 degree steps, measurements of 60 unique areas of the sample are enabled each separated by about 0.23 mm.

Another version could include two sequential rotating glass optics, similar to the single optic shown in FIGS. 3A and 3B allowing full translational control in the X and Y directions on the sample rather than just being limited to a circle. In still other designs, a composite glass translation optic could be used to reduce or eliminate refractive index dispersion effects which might result in small differences in translation verses wavelength.

One of the advantages of the geometries of FIGS. 1-3B is that the LIBS laser and the optical emission detection optics of the detector subsystem stay aligned on the same sample point as the sample location is modified by the movable optic.

Controller subsystem 12 is typically configured (e.g., programmed) to energize (e.g., pulse) the laser producing a series of laser pulses and to analyze the sample at one location by processing the output of the spectrometer between pulses. The controller subsystem is typically configured to receive a trigger signal (generated by the operator pushing a physical or virtual button or the like) and in response to pulse the laser. The controller subsystem then adjusts the movable optic (14, FIG. 1; 16, FIGS. 2-3B) and again energizes the laser and analyzes the sample now at a different location. A typical controller subsystem of a hand held or portable device will typically display, on an output screen, the elements detected and, optionally, their concentrations.

Operating the laser in the "eye safe" wavelength range of 1.5 μm offers significant advantages to handheld LIBS analyzers. Handheld units are by design open beam meaning the laser beam exits the unit before striking the sample. Therefore, scattered laser light (or direct laser light in the case of extreme misuse) could strike the user's eye. However because laser light at this wavelength is strongly absorbed by water, the laser light cannot reach the retina. The laser is therefore rated as low as a Class 1 depending on total energy. A Class 1 rating in particular is a significant commercial advantage as it eliminates the requirement of special safety glasses be worn during usage and regulatory requirements are greatly reduced compared to the most regulated Class 4 type of lasers. An eye safe laser may be preferred (e.g., class 1 or 2) and a safer laser source can be used in some embodiments (e.g., class 3) with the understanding that the class of laser and safe rating depends on variables such as energy level, wavelength, pulse width, pulse rate, divergence angle, and the like.

However, lasers that operate in the "eye safe" wavelength range near 1.5 μm create a number of hurdles, addressed below, that are needed to make this type of laser practical.

The LIBS technique requires that a burst of laser light strikes a sample, and deposits enough heat in the area struck so as to generate a plasma. When the plasma cools, electrons from the various elements that comprise the sample fall from various excited states to lower energy states, emitting photons in the process. The frequency of the emitted photon is proportional to the energy of the photon which is, in turn, equal to the difference between the two energy states. The frequency (or its inverse, wavelength) and intensity of the photons are measured by a spectrometer type detector to determine chemical composition of the sample spot where the plasma was created.

Portable or handheld LIBS systems are designed to operate from batteries and therefore are limited in power. If a portable or handheld LIBS system also uses an eye-safe laser, the energy available in the laser, at least with currently available technology, is further reduced. In order to generate a sufficient energy density for plasma ignition in the sample region being analyzed under these conditions, the laser is preferably focused down to a much smaller spot size than required for higher power bench top lasers, e.g., on the order of 5 μm-100 μm by lens 14, FIGS. 1-3B. The initiation of a plasma is dependent mainly on power density rather than total power. Therefore, a lower power laser must be focused to a smaller spot size to attain sufficient power density for plasma ignition. It is therefore possible to use a much lower powered laser that is more conducive to a handheld or portable LIBS unit and yet still generate a plasma on the sample surface. The main tradeoff of lower power lasers is that the ablation area on the sample will be reduced in area resulting in a more localized measurement and a lower signal.

A small sample area (5 μm-100 μm in diameter) does however create problems that should be solved to use a portable or handheld LIBS device for real-world applications. First, it can be important that the laser be focused at the location where the analysis is required. For most samples, this is the surface of the sample. A small deviation in the focus position for whatever reason means the laser is focused slightly above the sample surface, yielding incomplete plasma formation, or the laser light strikes the surface before reaching the focal point (which theoretically is at some depth inside the sample in this case). In either case, an incomplete plasma is formed with poorer light formation or the plasma is not representative of the sample being tested leading to erroneous analytical results. Also, in many real-world cases, samples being tested are not completely smooth or they are not flat (such as wires, tubes, rods, etc.). In these cases the ideal focus may vary from sample to sample such as testing a flat piece of steel followed by testing a ¼" diameter steel rod or a ⅛" welding rod or wire. Adjustable focusing lens 14, FIGS. 1-3B under the control of controller 12 also allows for proper focusing in samples with features which block or interfere with the head of the portable device.

The second issue is sample cleanliness. LIBS is a very sensitive technique and the depth of the region being analyzed is typically just several microns, coupled with a sample area diameter of 5-100 μm. It is therefore important that the surface being analyzed is representative of the sample and is therefore free of dirt, oils and/or oxidation. Prior to taking spectral data to determine composition, it is typical to fire a number of "cleaning shots" with the laser. These cleaning shots burn off material on the surface allowing underlying clean material to be analyzed. However, as stated above in order for the cleaning tests to be effective, the laser must be properly focused as well. In battery powered devices, it is important not to fire cleaning shots which are not required in order to conserve both battery power and analysis time.

A third issue is sample inhomogeneity. For certain types of samples such as vacuum melt alloys, the samples are likely very homogeneous over a 50 µm-100 µm laser beam spot size. However for geochemical samples (soils, sediments, ores) or liquid suspensions (as a few examples), it is likely that the concentration of the sample changes over a 5 µm-100 µm sample area. Therefore, it can be important to fire the laser at several different locations on the surface of the sample and to average the results.

In embodiments of the invention, translating mechanism 22, FIGS. 1-3B moves the focusing lens 12. At the first scan location, the laser is fired and a spectrum from the sample is acquired. A typical spectrum that shows intensity of light measured versus wavelength is shown in one or more of FIGS. 4A-4C. The entire spectrum or one or more regions of the spectrum as output by the spectrometer are integrated by the controller 12, FIGS. 1-3B. The lens 14 is then moved incrementally through a series of positions causing the laser focus to occur in front of the sample and then progressing into the sample bulk. Intensity data is gathered and stored for each focus position. The lens may be moved from a furthest away position to a closest position (a typical range of about 6 mm) in 0.01-1 mm increments.

Figure 4A:
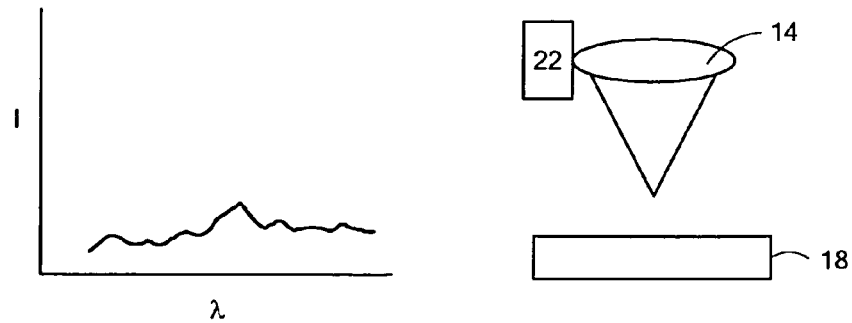
FIGS. 4A-4C are schematic views showing sample spectral intensity data as determined by a detector subsystem in accordance with FIGS. 1-3B at three different focusing lens positions for a technique used to determine the optimal focusing lens position in accordance with examples of the invention.
Figure 4B:
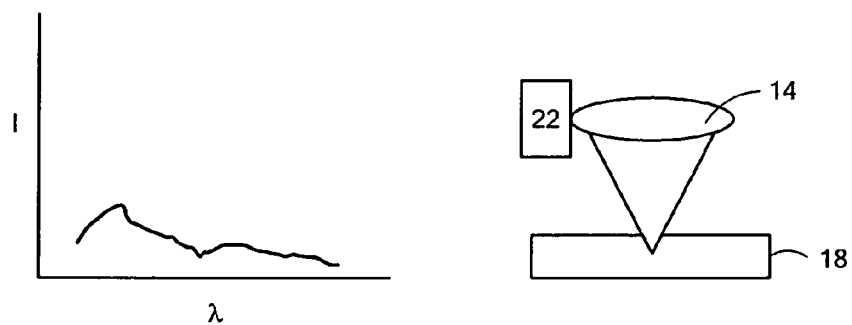
Figure 4C:
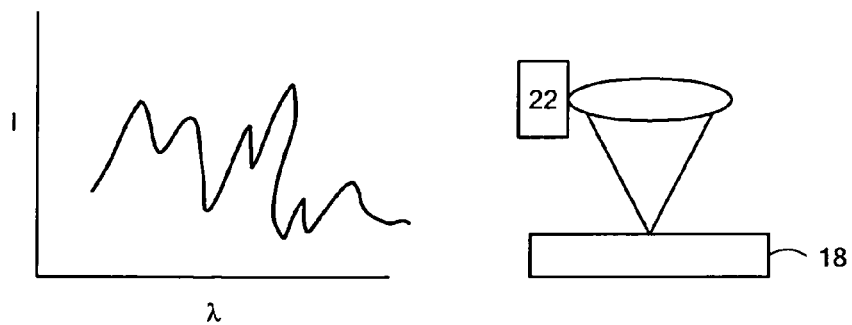

FIG. 4A shows the intensity data where lens 14 is too far away from sample 18; FIG. 4B shows the intensity data where lens 14 is too close to sample 18; and FIG. 4C shows the intensity data when the lens 14 is producing a preferred, optimum spot size (e.g., 50-100 µm) on the surface of sample 18. In FIG. 4C, the intensity is at a maximum. Controller 12, FIGS. 1-3B, is programmed to detect a maximum or near maximum intensity by adjusting the lens focus from outside to inside the sample. The information is then available to the controller on where the lens should be positioned for both large cleaning pulse spots and smaller spots to be used for data collection.

Figure 5:
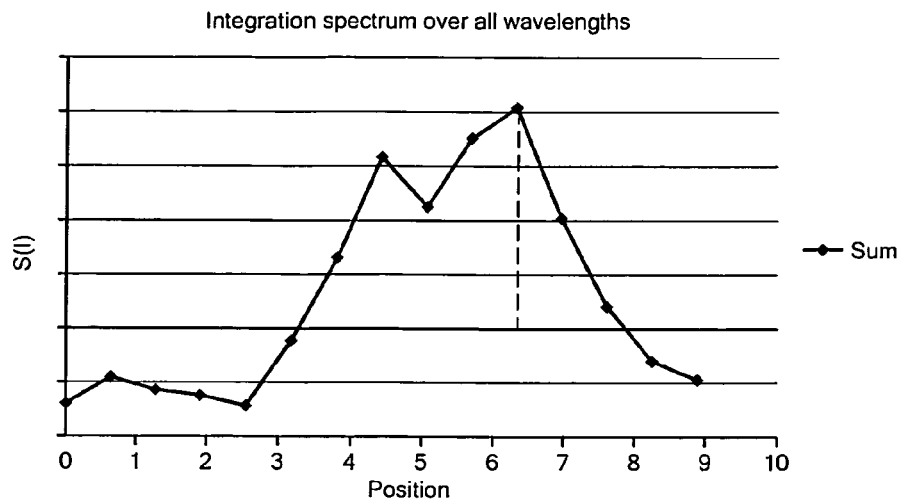
FIG. 5 is a graph showing the integration of spectral intensity over all wavelengths for ten different focusing lens positions.

An example of data from a carbon steel sample is shown in FIG. 5. The integrated intensity will approach a peak value at the correct optimal focal location as shown for position 6 in one or more of FIGS. 4A-4C. For the data shown, the increments were in steps of 600 µm movement for the focusing lens, although the step size can be made smaller. Therefore, when a sample is placed in front of the device, the first step is that spectra are gathered at several focusing lens locations in order to automatically fine tune the focal spot of the laser on the sample. Controller 12, FIGS. 1-3B is configured to perform these steps as part of the initial testing and to determine and save the focusing lens location that yielded the maximum intensity. After the optimal focusing position is determined automatically, the processor moves the lens to this location and may then begin testing the sample or optionally, moves the lens to create a larger than optimum spot size for the purposes of cleaning, followed by data collection at the optimum (smallest) spot size. The controller is preferably configured to perform this task automatically rather than requiring operator input and judgment.

Without a process to automatically focus the laser onto the sample, the operator may not know if the sample results were correct. The concentration results determined by the instrument are related to the intensity of light measured in specific regions of the spectrum. If the laser is not properly focused, the concentration results will be inaccurate. For a commercially viable product, it is desirable that the instrument automatically determine the correct focusing location for the laser. Otherwise, an operator would have to manually perform measurements to make this determination. This may require a far higher skill level operator and therefore could diminish the commercial success of the LIBS device.

A next step in the analysis is to automatically determine if the sample location being tested is sufficiently clean. One cleaning cycle method is to take multiple repeat laser tests of the area and identify two (typically) of the largest spectra (atomic emission) peaks using available peak finding algorithms. Smaller peaks may also be selected that are important to the analysis at hand. These peaks correspond to particular elements present in the sample area being tested. Additional laser tests of the sample area are performed. Controller 12 then computes a rolling average of the intensity measured for the above two elements. When the intensity stops changing by less than a predetermined percentage from each point in the rolling average (for example by less than 5%), then the sample is appropriately cleaned. An alternative method for determination of cleanliness would be to compute the intensity ratios of the rolling averages. Once the ratio stabilizes to within a preset percentage, the sample may be considered to be clean.

Figure 6A:
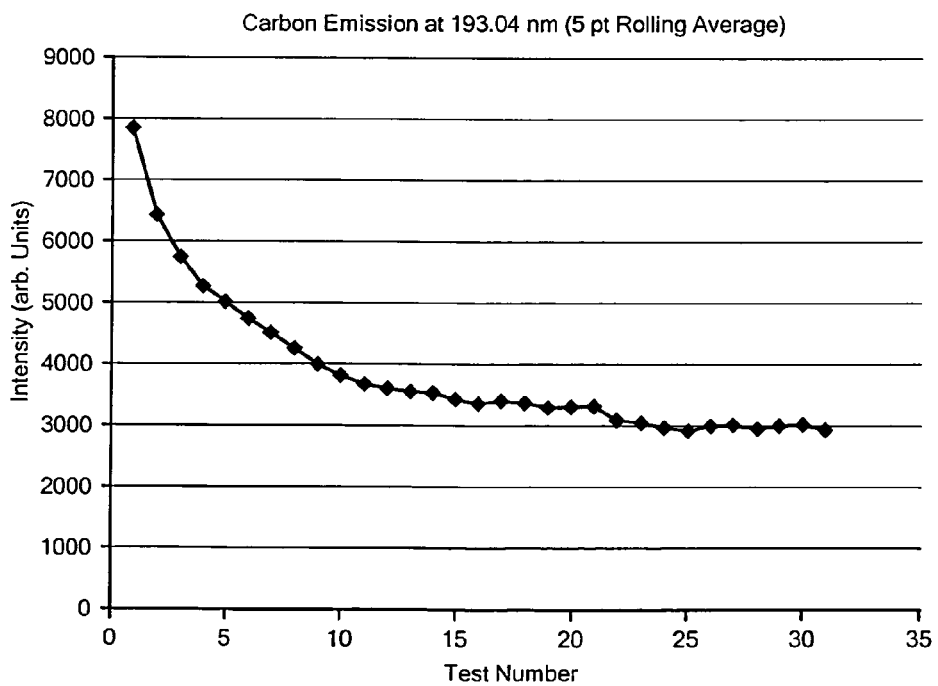
FIG. 6A is a graph showing intensity for carbon in a steel sample during sequential laser pulses in accordance with a cleaning method associated with embodiments of the invention.
Figure 6B:
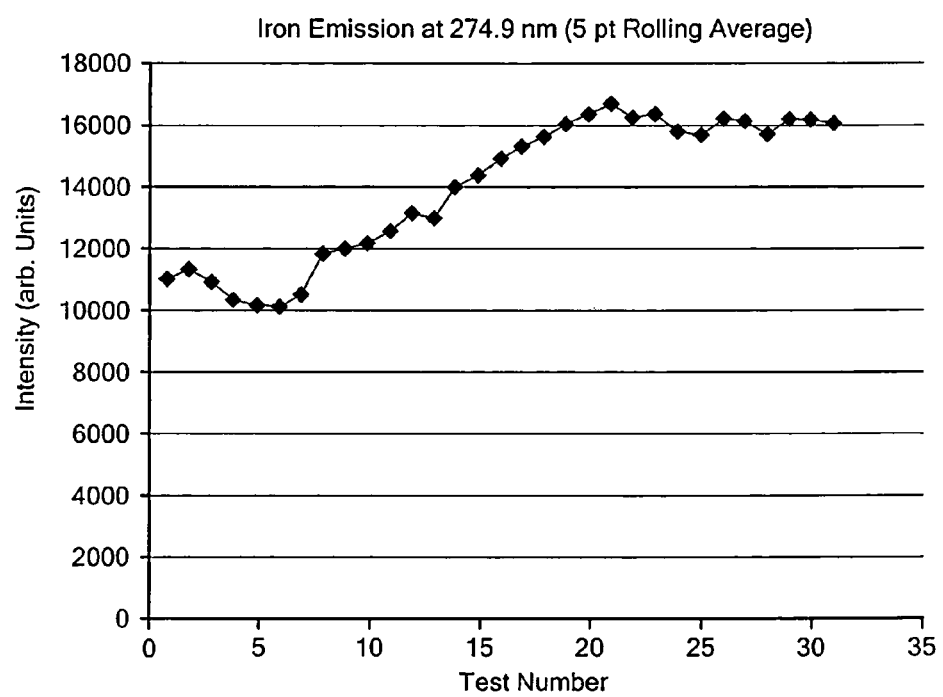
FIG. 6B is a graph showing intensity for iron during sequential laser pulses in accordance with the cleaning method associated with FIG. 6A.
Figure 7A:
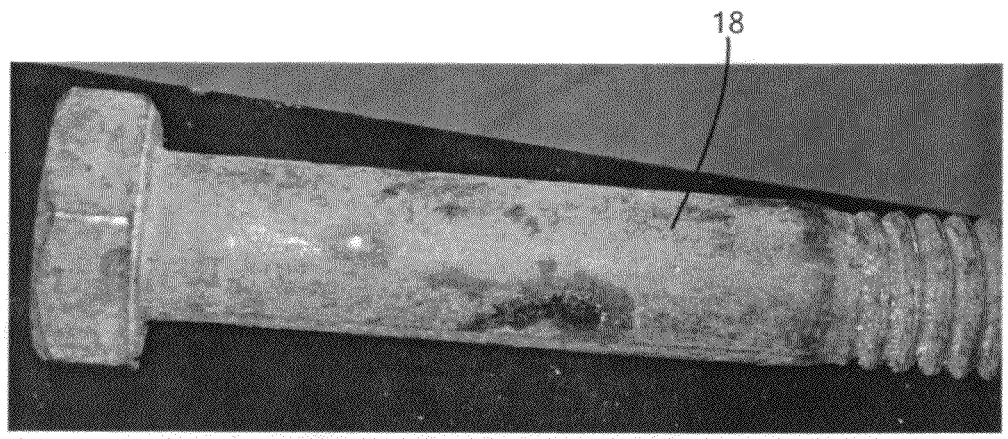
FIG. 7A is a view of a sample to be cleaned by the LIBS laser of FIGS. 1-3B prior to performing an analysis.
Figure 7B:
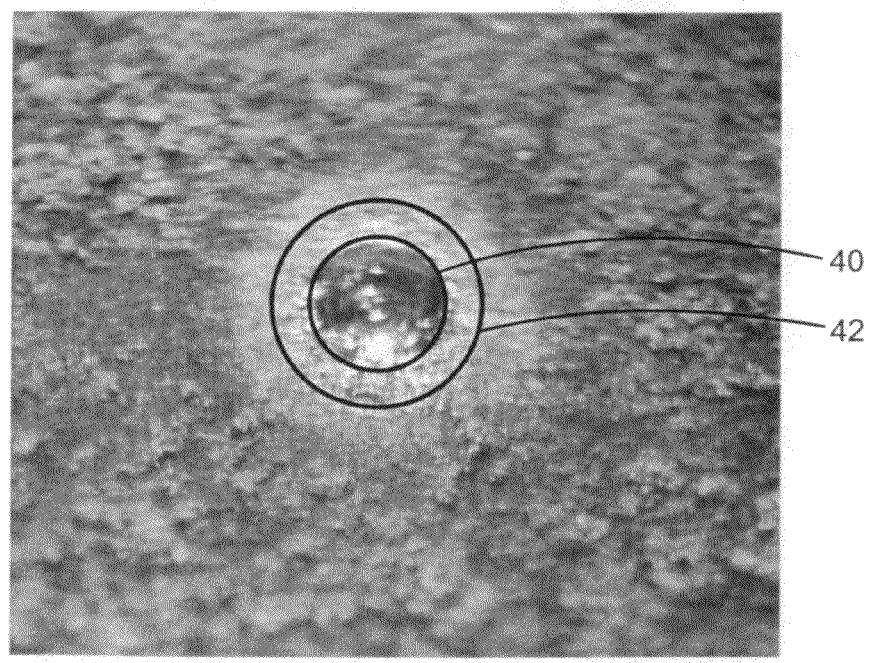
FIG. 7B is a view of a portion of the sample of FIG. 7A after cleaning.

An example of peak intensity verses cleaning pulse count is shown in FIGS. 6A and 6B for a sample of rusty carbon steel (photo in FIGS. 7A-7B). The cleaning cycle requires that a layer of dirt and oxidation be burned off by the laser blasts. As shown, the intensity of the carbon peak (FIG. 6A) and iron peak (FIG. 6B) change with sequential tests (laser pulses) until the results approach a stable intensity level. Here, 25 laser pulses resulted in a stabilized detector output. The method in this case may use a five point moving average. The carbon intensity (FIG. 6A) decreases with the sequential cleaning tests as carbon-containing organic material (i.e. dirt, oils or skin oils) are burned of the sample. The point at which the carbon intensities stop decreasing indicate that only the base metal is being tested.

Likewise, the iron concentration (FIG. 6B) increases during the early cleaning tests as oxidation and other materials are burned off which were masking the iron content in the sample. Again, as the change in intensity of the iron photon emissions flatten with increasing test number, the base iron in the sample is being analyzed.

In principle, it may possible to only use a single peak for the automatic determination of when to end the cleaning tests. In addition, when testing for low concentrations of an element, say 1% carbon in 99% iron, the carbon line will be far more sensitive to cleanliness than the iron since the ratio of contamination to sample carbon is large and the ratio of contamination to iron is small. The peaks which are selected for analysis may include typical elements in the bulk sample or in the contamination coating such as carbon, oxygen, and silicon. By automatically stopping the cleaning cycle when the sample is sufficiently clean, battery power is conserved and testing time is reduced.

It should be noted that the process of finding the optimal focal length for the sample, described above, also provides some cleaning of the sample spot, thereby reducing the number of cleaning tests performed in this step.

One preferred cleaning method also results in an optimal manner to perform the cleaning and the subsequent sample analysis. Based on the testing performed to develop this method, a number of observations were made about the sample cleaning. Consider the pictures of a sample shown in FIGS. 7A and 7B. Upon examination of the area struck by laser, it was observed that the inner portion of the circular laser spot area 40, FIG. 7B, is well-cleaned but near the perimeter 42 of the analysis area, the cleaning may be less thorough.

In the real world of non-ideal lenses, lasers, and diffraction limited optics, it is expected that the inner component of the laser beam will deliver more energy to the sample than the outer perimeter of the beam. The region of the sample will thus be better cleaned more towards the center of the sample area. Therefore, an additional embodiment of the cleaning cycle method is to clean a larger area, in one example, than is actually analyzed. After the controller determines the optimal laser beam focal length as described previously, the focusing lens is moved such that the beam striking the sample surface during cleaning tests is about 20% larger. See, e.g., FIG. 4B. When the controller determines that the sample region is adequately cleaned, according to the above described steps, then the controller returns the focusing lens to the optimal position previously determined and stored. This assures that the area struck by the laser during analysis is therefore smaller than the area cleaned assuring that the area to be analyzed is thoroughly cleaned.

Another problem addressed is sample non-homogeneity. Many samples, for example geochemical samples encountered in the analysis of soil, ores, sediments and/or slurries are not homogeneous across the sample face. In other techniques, such as x-ray fluorescence analysis, the samples are collected and ground to about a 100 µm particle size prior to analysis. However, 100 µm is approximately the same size as the laser beam on the sample in the case of a LIBS analysis in accordance with embodiments of the invention. It is therefore desirable to test multiple locations on the sample and average the results.

The method provides for an optical/mechanical means which moves the laser beam spot across the sample as discussed with respect to FIGS. 1-3B to address the problem of non-homogeneous samples. FIGS. 3A-3B, for example, show an optical component 16 that is angled with respect to the laser beam striking it. As the optical component rotates by discrete amounts, the laser beam is directed to different locations on the sample. Therefore, a preferred method used locates the laser beam at a particular spot on the sample, finds the correct focal length by translating the focusing lens 14, and then performs the cleaning operations as described above, followed by the sample analysis. The optical component 16 is then rotated a discrete amount, for example 60 degrees, to yield a different sample location which it is also cleaned and analyzed. At each location, the optimal focus is determined and saved for the laser spot on the sample as described above. In a further embodiment, if the analytical results (e.g., the concentration of the top five elements changes by 10% or less) for a second or third testing location are not appreciably different than the first testing location, the controller terminates the measurement process and the controller averages the results. Thus, for homogeneous samples, only two to three locations are cleaned and analyzed conserving power in a battery operated device. For non-homogeneous sample, five locations may be cleaned and analyzed. The controller is preferably configured to report to the operator when the sample is homogeneous and/or non-homogeneous. Note that XRF techniques are not able to determine if a sample is non-homogeneous.

Figure 8:
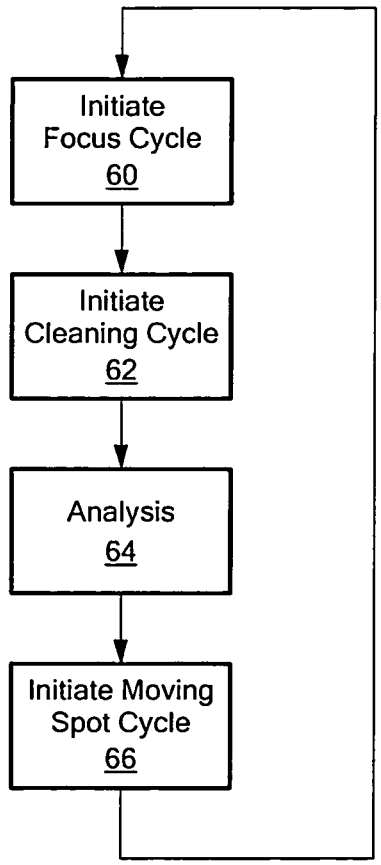
FIG. 8 is a flow chart depicting the primary steps associated with a method in accordance with the invention and/or the programming and/or configuration of the controller depicted in FIGS. 1-3B.
Figure 9:
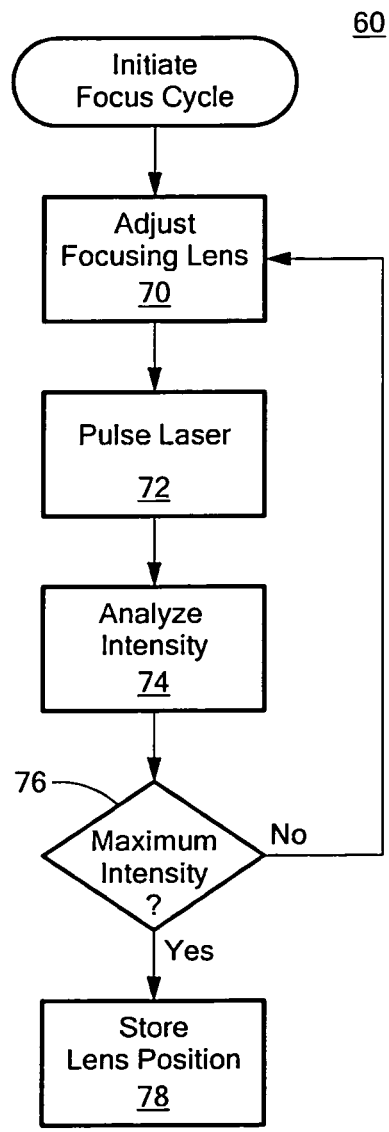
FIG. 9 is a flow chart depicting the primary steps associated with the focusing cycle depicted in FIG. 8.

FIG. 8 depicts the processing of controller 12, FIGS. 1-3B in one preferred embodiment. The focusing cycle is initiated, step 60, in response to a trigger signal followed by the cleaning cycle, step 62, for each sample location. These cycles may be reversed. At each location on the sample, the spectrum analysis is performed, step 64, wherein the elemental concentrations are computed, reported, and typically saved. The hand held portable unit, see FIG. 12, preferably has a display screen for displaying the elements present in the sample, their concentrations, and other data. In general, the controller subsystem is configured, (e.g., programmed) to pulse the laser producing a series of laser pulses and to process the resulting signals from the detector (spectrometer) subsystem to determine one or more elemental concentrations in the sample. For LIBS analysis, the detector outputs signals representing intensities at different wavelengths defining the elements in the sample and the various concentrations.

The laser beam spot is then moved, step 66 whereupon the focusing, cleaning, and analysis cycles repeat for the new sample location. Sequential locations are thus analyzed.

In the focusing cycle, the controller is configured to adjust the focusing lens, step 70, pulse the laser, step 72, and analyze the intensity data reported by the detector electronics, step 74 (see FIGS. 4A-4C) until an optimum intensity is detected (which is at or near the maximum), step 76. The lens position which resulted in the optimum intensity is stored, step 78. A memory accessed by the controller may be used to store lens position values, calibration constants, spectral data, algorithms, computer code, and the like. FIG. 5 demonstrates an optimum focus location in the range of positions 4 to 7.

Figure 10:
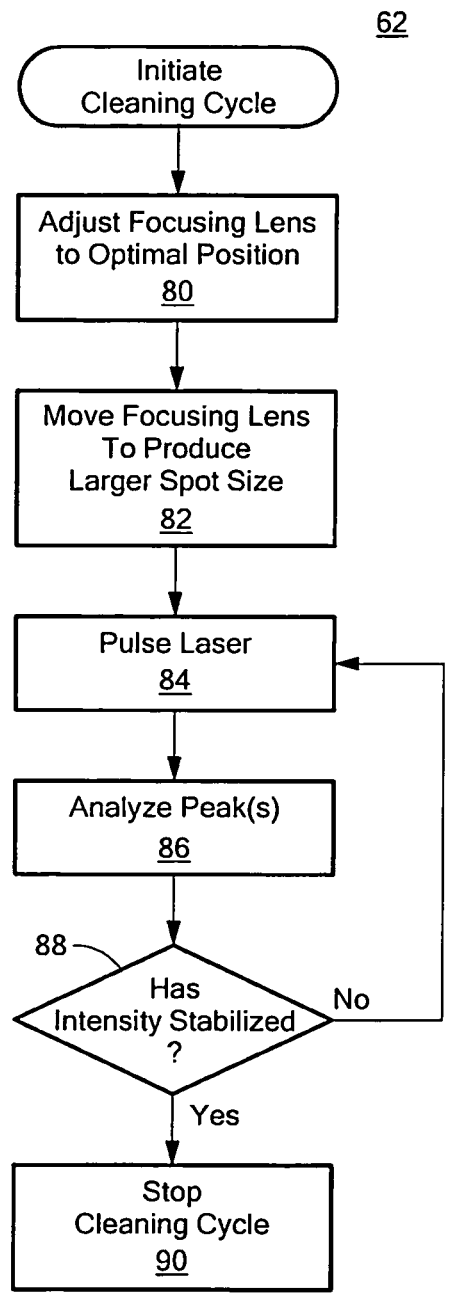
FIG. 10 is a flow chart depicting the primary steps associated with the cleaning cycle of FIG. 8.

In the cleaning cycle, FIG. 10, the focusing lens is moved to the optimal position, step 80, or optionally moved to produce a slightly larger spot size, step 82. The laser is repeatedly pulsed, step 84, and for each resulting plasma, one or more peaks are analyzed, step 86. The cleaning cycle stops when the intensity data indicates the intensity has stabilized, step 88 and 90 as shown in the example of FIGS. 6A and 6B.

Figure 11:
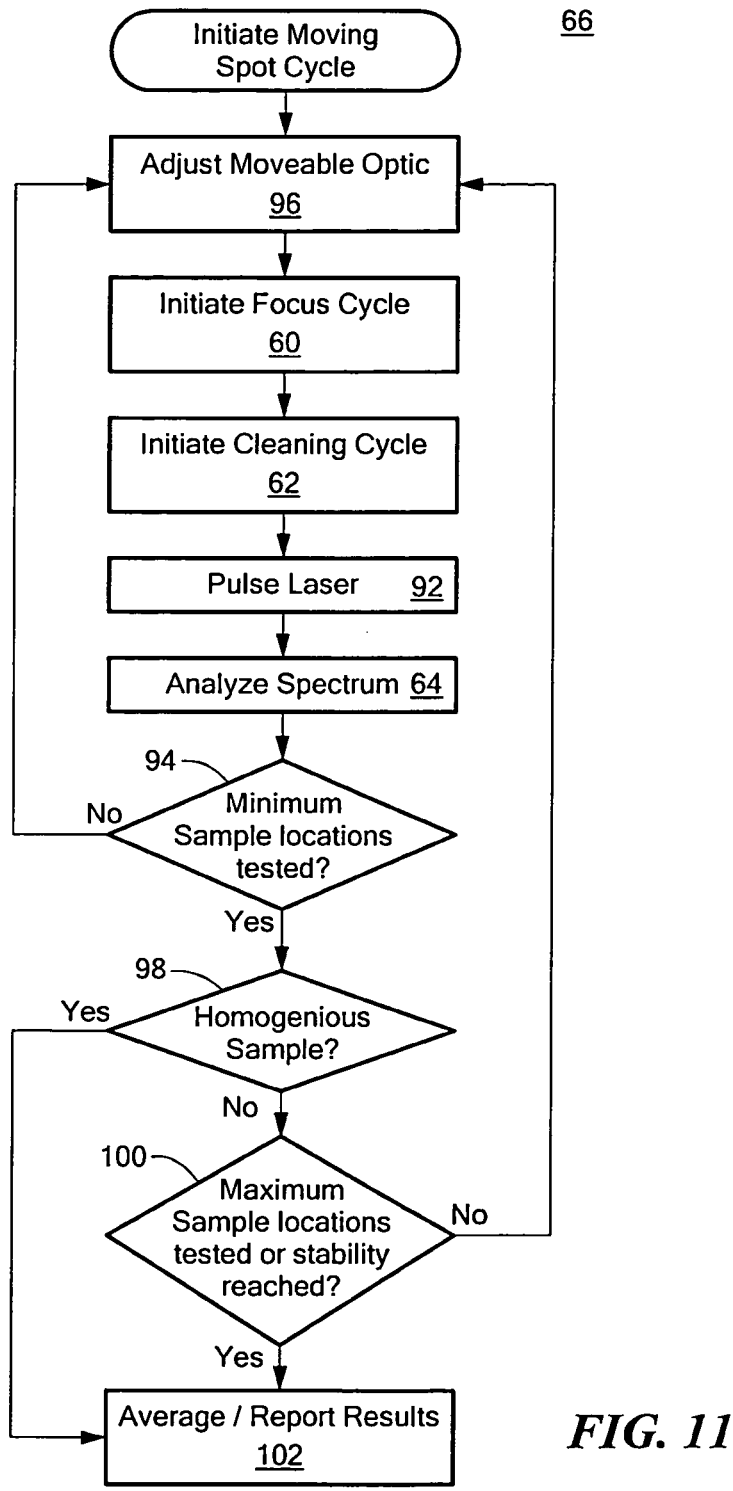
FIG. 11 is a flow chart depicting the primary steps associated with the moving spot cycle shown in FIG. 8.

The moving spot cycle, FIG. 11, preferably includes running the focusing cycle, step 60 and running the cleaning cycle 62 at each location on the sample. At the optimal laser spot size, the laser is pulsed, step 92 and the spectrum is analyzed, step 64. Typically, a minimum number of sample locations are tested (e.g., 3), step 60 as depicted at 94 and if the minimum number has not been reached, the movable optic (14, FIGS. 1-3B, 16) is adjusted to move the beam to a different location on the sample, step 96, FIG. 11. The focusing, cleaning, and analysis cycles are again repeated for this new sample location until the analysis as between different sample locations indicates a homogeneous sample as shown at 98 or a maximum number of sample locations (e.g., 5) have been tested, step 100 (for non-homogeneous samples). Alternatively, once the sample is determined to be non-homogeneous, a predetermined number of new sample locations may be analyzed. Preferably, the results are averaged for both homogeneous and non-homogeneous samples and reported, step 102.

The number of required sequential sampling locations may depend on how heterogeneous the sample is. It is desirable to minimize the required sampling time, so various algorithms may be employed as data is collected to optimize the sampling time required. One algorithm starts with a minimum sampling location count (3 locations for example) to establish a baseline variance or standard deviation in constituent concentration. If the standard deviation is above a pre-set threshold, then the algorithm will initiate further measurements from additional sample N locations.

Each time a new location is sampled, the standard deviation of the data set is calculated. The precision of the mean (or average) concentration is related to the standard deviation and the number of samples N in the data set by:

$$\sigma_{mean} = \frac{\sigma}{\sqrt{N}}. \tag{1}$$

The "standard deviation of the mean" is a measure of how stable the computed average of the measured concentrations are. The algorithm terminates further sample location measurements once the standard deviation of the mean is below a pre-set threshold. Often with such algorithms, a maximum sample location count is programmed to force the instrument to stop measuring after a certain time limit is reached. Such algorithms can also make estimates of time to completion based on the rate of improvement of the "standard deviation of the mean" (or similarly computed indicator) after the first several measurements. The user may be given the option to wait for completion or to stop the measurement.

Figure 12:
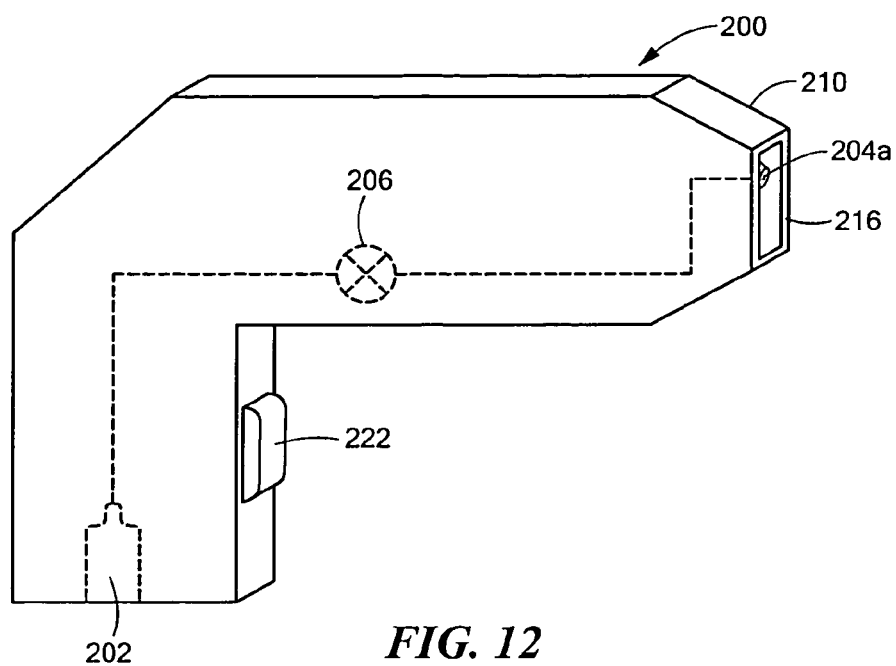
FIG. 12 is a schematic three dimensional view of a hand held battery powered LIBS spectrometer device in accordance with an example of the invention featuring a gas purge subsystem.

FIG. 12 shows a handheld portable unit housing the subsystems and components of FIGS. 1, 2, and/or 3B and with the associated electronic circuitry carrying out the analysis, signal processing, and control steps depicted above with respect to FIGS. 4A-6B and FIGS. 8-11.

An argon purge subsystem may be included for better analysis of the sample for certain elements including sulfur, phosphorous, and/or carbon.

In some embodiments, the focusing lens adjustment cycle is performed without moving the laser spot to multiple locations on the sample and vice versa. The cleaning cycle is, in some embodiments, preferred and in another aspect is optional and/or separately patentable.

In one preferred embodiment, the hand held LIBS spectrometer is battery powered and employs an eye safe laser. The automatic focusing steps ensure repeatable, more accurate elemental concentration results without operator intervention. Automatic focusing provides more repeatable results, without operator intervention, and more accurate results.

The cleaning cycle ensures that the laser adequately cleans the sample while at the same time saves testing time and battery power because, once the sample is adequately cleaned, no more cleaning laser pulses are needed. This reduces the number of laser shots and therefore makes the test conclude faster and saves battery power.

Adequate sampling of all samples is performed and battery power and testing time are conserved.

Figure 13:
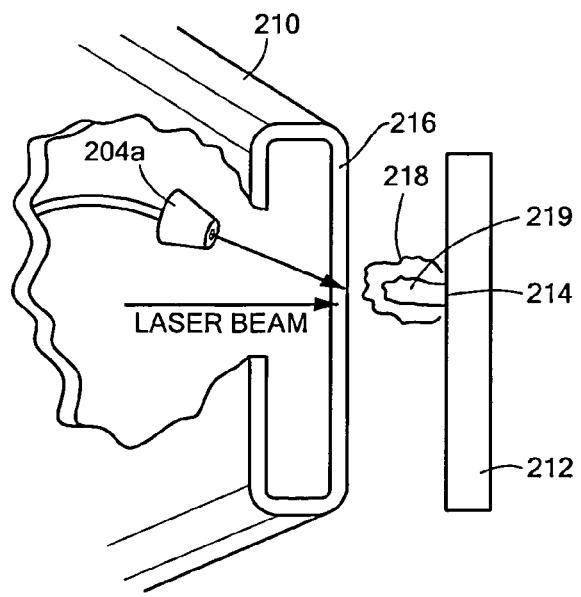
FIG. 13 is a schematic view showing a portion of the device of FIG. 12.

FIG. 12 shows one example of a battery powered, portable LIBS analyzer 200 with gas (e.g., argon) cartridge 202 loadable therein. As shown in FIG. 13, one or more nozzles 204a is fluidly connected to cartridge 202 via valve 206, FIG. 12. In other examples, a cartridge or small tank is connected to unit 200 and carried in a small pack for field analysis.

Preferably, only a small supply of argon is required in the purge subsystem because the nozzle(s) is configured to deliver a small spray of argon gas locally in a small purge volume. Unit 200 may have a converging front nose 210 where the laser beam exits to strike sample 212 at location 214 (e.g., 5-100 μm in diameter) creating a plasma 219. Nozzle 204a is just inside distal nose 210 proximate end wall 216 and oriented to produce an argon spray at (and preferably only at) location 214. The nozzle has an orifice configured to produce a purge volume of argon gas less than 1.0 cm$^3$, typically as small as 0.5 cm$^3$ as show at 218 so it just surrounds the plasma 219 and little argon is wasted. In one example, the argon gas volume was 0.125 cm$^3$. As discussed below, the flow rate is low and the argon purge is used only when needed in order to further save argon resulting in a WS analysis unit which does not require a large supply of inert gas.

Figure 14:
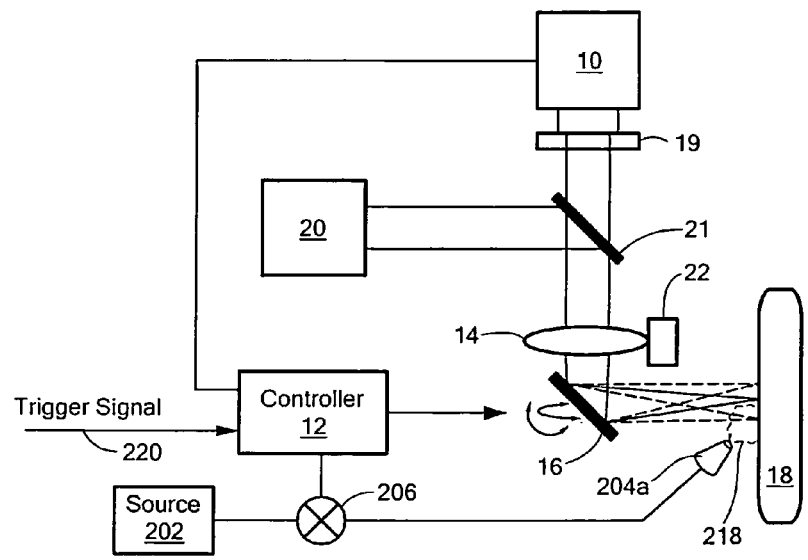
FIG. 14 is a block diagram showing the primary components associated with an example of a gas purge subsystem.

FIG. 14 shows controller 12 controlling solenoid valve 201 between source 202 and nozzle 204a. A trigger signal as shown at 220 (generated, for example, by pressing on trigger mechanism 222, FIG. 12) is received at controller 12 and, in response, controller 12 may optionally initiate the cleaning cycle as discussed above. Another trigger mechanism may include a physical or virtual button.

Figure 15:
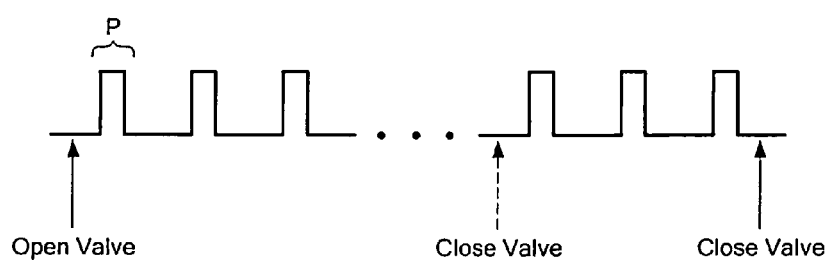
FIG. 15 is a timing diagram showing a number of laser pulses.
Figure 16:
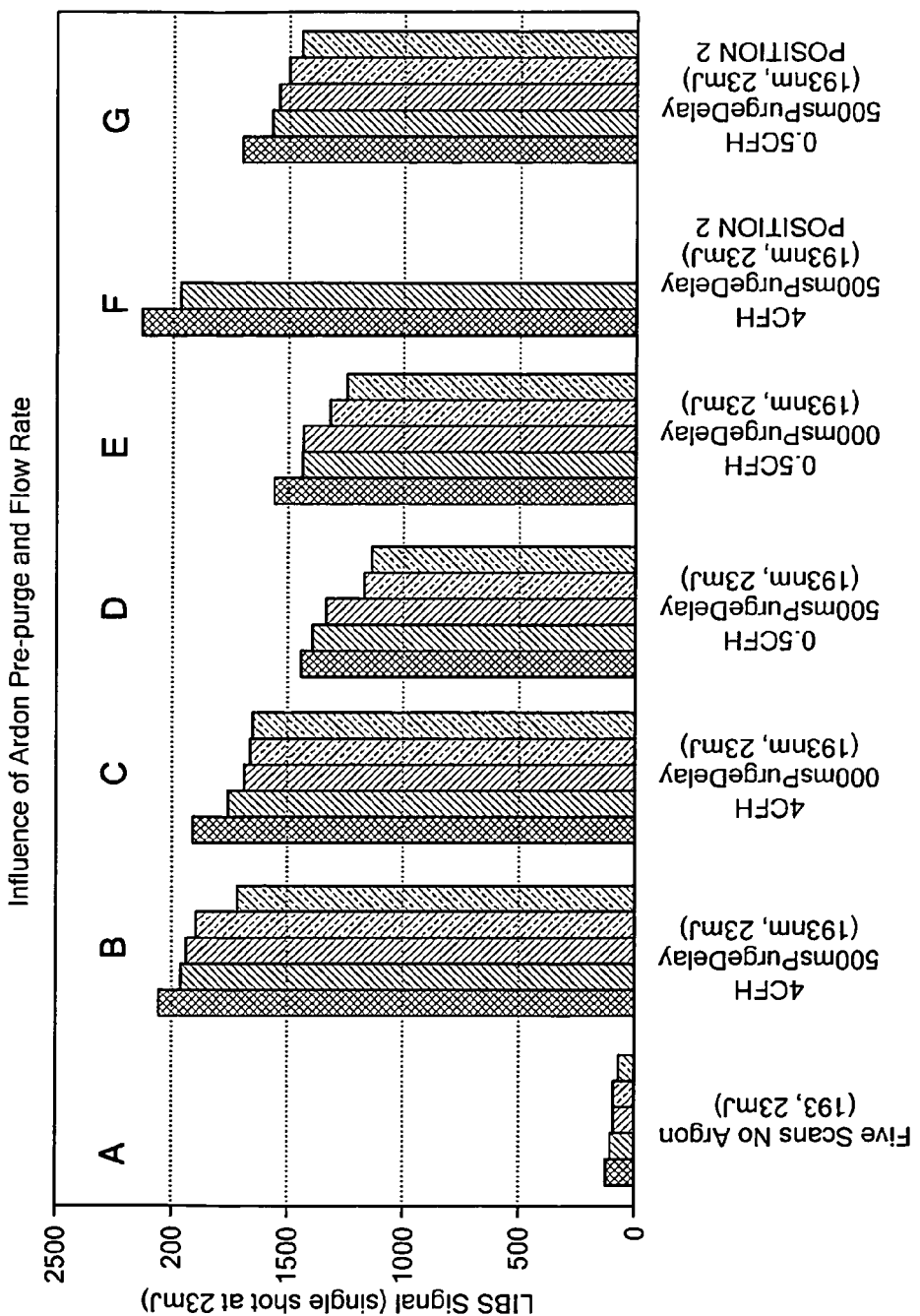
FIG. 16 is a graph showing the spectrometer signal strength for a number of purge conditions.

During the subsequent analysis cycle, controller 12 opens valve 206 just prior (e.g., 0.1-0.5 seconds before) the first plasma producing laser pulse as shown in FIG. 15. FIG. 16 shows a strong signal for carbon in a test sample even when the purge occurred just 0.1 seconds prior to the first laser pulse. Controller 12, FIG. 14 is further configured to close valve 206 shortly after the last laser pulse or even prior to the last laser pulse as shown in FIG. 15 in order to conserve the purging gas.

FIG. 16 depicts the influence of the flow rate, nozzle position, and purge timing on the resulting LIBS signal output by spectrometer 20, FIG. 14. In test A, no purge was used and the carbon peak was difficult to correctly decipher. In test B, the purge rate was 4 CFH, the nozzle was 0.2 cm away from the sample and the plasma location, and the purge gas was initiated 0.5 seconds before the first laser pulse. In test C, the nozzle position and the flow rate were the same as in test B but now the purge gas was initiated only 0.1 second before the first laser pulse. The signal strength was still very high. In test D, a lower flow rate of 0.5 CFH was used and the purge occurred 0.5 seconds before the first laser pulse while in test E the lower gas flow rate of 0.5 CFH was used and the solenoid valve was opened for a purge 0.1 seconds before the first laser pulse. In both cases, the signal strength was sufficiently high. In test F and G the nozzle was brought closer to the sample (0.1 cm away from the sample). In test F a flow rate of 4 CFH was used with a 0.5 second purge delay and in test G a 0.5 CFH flow rate was used with a 0.5 second purge delay.

Accordingly, it is possible to use a very low flow rate of 0.5 CFH and a very short (0.1 second) delay before the first laser pulse and still obtain a sufficiently strong signal from the resulting photons. A purge rate of less than 2 CFH may be optimal.

In one typical scenario, the output of spectrometer 20 is analyzed between the laser pulses shown in FIG. 15. In some examples, if the valve can be actuated at a high frequency rate, the gas can even be turned off between laser pulses and then on again just prior to each laser pulse.

Thus, in one preferred embodiment, an improved signal is generated and detected by the spectrometer using an inert gas purge. The gas is conserved by using a low flow rate and a smaller size nozzle properly located and oriented to produce a small volume purge spray. And, the purge is used only when required. One result is the ability to use only a small cartridge as opposed to an unwieldy tank in a portable, hand held, battery powered system. When one cartridge is emptied, another full cartridge can be quickly loaded into the unit.

Other embodiments will occur to those skilled in the art and are within the following claims. One example includes a Raman laser and Raman spectroscopy.

What is claimed is:

1. A battery powered, portable LIBS analyzer comprising:
   a laser source generating a laser beam received by an adjustable focusing lens for creating a plasma at a location on a sample;
   a spectrometer responsive to photons emitted by the sample at said location and having an output;
   a cartridge of inert gas;
   a nozzle configured to deliver inert gas from the cartridge locally to said location on the sample;
   a valve between the cartridge of inert gas and the nozzle;
   a trigger mechanism generating a trigger signal; and
   a controller, responsive to the trigger signal, and configured to:

initiate a focusing cycle by pulsing the laser while adjusting the focusing lens based on said spectrometer output to focus the laser beam at one location on the sample, initiate a cleaning cycle to clean said location by pulsing said laser for a number of pulses based on the output of said spectrometer, initiate an analysis cycle by pulsing said laser while controlling said valve to purge said location with inert gas and analyzing said spectrometer output, move the laser beam to a new location on the sample, and repeat said cleaning cycle and said analysis cycle at said new location.

2. The analyzer of claim 1 in which said cartridge is loadable with the analyzer.

3. A method of operating a battery powered, portable LIBS analyzer comprising:

initiating a focusing cycle to adjust the focus of a laser beam on a sample at a location based on an output of a spectrometer;

initiating a cleaning cycle to clean said location by pulsing the laser for a number of pulses based on the spectrometer output indicating said location is sufficiently clean;

initiating an analysis cycle to analyze said location by pulsing said laser while purging said location with an inert gas and analyzing said spectrometer output;

moving said laser beam to a new location on the sample; and repeating the cleaning cycle and the analysis cycle at said new location.

* * * * *